United States Patent
Ghazwani et al.

(10) Patent No.: US 12,164,074 B2
(45) Date of Patent: Dec. 10, 2024

(54) INTERACTIVE CORE DESCRIPTION ASSISTANT USING VIRTUAL REALITY

(71) Applicant: SAUDI ARABIAN OIL COMPANY, Dhahran (SA)

(72) Inventors: Assad Hadi Ghazwani, Muharraq (BH); Mokhles M. Mezghani, Dhahran (SA); Mustafa Ali Al Ibrahim, Safwa (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 338 days.

(21) Appl. No.: 17/643,676

(22) Filed: Dec. 10, 2021

(65) Prior Publication Data
US 2023/0184981 A1 Jun. 15, 2023

(51) Int. Cl.
G01V 1/50 (2006.01)
G06T 19/00 (2011.01)

(52) U.S. Cl.
CPC .............. *G01V 1/50* (2013.01); *G06T 19/006* (2013.01); *G01V 2210/542* (2013.01)

(58) Field of Classification Search
CPC ... G01V 1/50; G01V 2210/542; G06T 19/006
See application file for complete search history.

(56) References Cited

U.S. PATENT DOCUMENTS

| 8,447,524 B2 | 5/2013 | Chen et al. |
| 9,277,367 B2 | 3/2016 | Hymel |
| 9,645,785 B1 | 5/2017 | Hannaford et al. |

(Continued)

FOREIGN PATENT DOCUMENTS

| CA | 2984190 A1 | 4/2019 |
| FR | 3068381 A1 | 1/2019 |

(Continued)

OTHER PUBLICATIONS

Al sa'adi, A. "How Saudi Aramco is digitalizing its operations" Oil and Gas Middle East; Feb. 12, 2020; Retrieved from the Internet: URL: https://www.oilandgasmiddleeast.com/products-services/36150-how-saudi-aramco-is-digitalising-its-operations (13 pages).

(Continued)

*Primary Examiner* — Manish S Shah
*Assistant Examiner* — Sharad Timilsina
(74) *Attorney, Agent, or Firm* — Osha Bergman Watanabe & Burton LLP

(57) ABSTRACT

A method for generating a core description is disclosed. The method includes coring and collecting rock cores from geographical locations in the subterranean formation, detecting, using an augmented reality (AR) device worn by a user, content of an identifying tag of a rock core within a device view of the AR device to identify a well where the rock core is obtained, retrieving, by the AR device from a data repository, historical data of the well, activating, by the AR (Continued)

device, a sensor to acquire additional data from the rock core to supplement the historical data, and presenting, by the AR device, an AR image including a first image of the historical data and the additional data superimposed over a second image of the rock core, where the user generates the core description based on viewing the AR image.

20 Claims, 6 Drawing Sheets

(56) References Cited

U.S. PATENT DOCUMENTS

| | | | |
|---|---|---|---|
| 9,670,753 | B2 | 6/2017 | Filippov et al. |
| 9,677,840 | B2 | 6/2017 | Rublowsky et al. |
| 10,366,543 | B1* | 7/2019 | Jurgenson ............ G06F 3/04815 |
| 2010/0324868 | A1* | 12/2010 | Russell .................... B28D 1/22 83/53 |
| 2015/0186730 | A1 | 7/2015 | Hannaford |
| 2016/0259404 | A1 | 9/2016 | Woods |
| 2017/0004650 | A1* | 1/2017 | Caliskan ................... G06T 7/00 |
| 2019/0362556 | A1* | 11/2019 | Ben-Dor ................. G06F 3/167 |
| 2020/0174157 | A1* | 6/2020 | Teh .......................... E21B 43/00 |
| 2020/0192467 | A1* | 6/2020 | Capgolu ............... E21B 47/002 |
| 2020/0264433 | A1* | 8/2020 | Zhong ............... G02B 27/0093 |

FOREIGN PATENT DOCUMENTS

| | | |
|---|---|---|
| GB | 2501567 A | 10/2013 |
| KR | 20110136018 A | 12/2011 |

OTHER PUBLICATIONS

Saudi Aramco "What is digital transformation?" Saudi Aramco website; Apr. 2021; Retrieved from the Internet: URL: https://www.aramco.com/en/creating-value/technology-development/in-house-developed-technologies/digitalization (9 pages).

Chang O. "Application of Mixed and Virtual Reality in Geoscience and Engineering Geology" D. Sc., Simon Fraser University; 2018 (218 pages).

Savjani R. "4 ways Hololens will revolutionize the oil drilling and exploration industry" Softweb Solutions; Jan. 25, 2017; Retrieved from the Internet: URL: https://www.softwebsolutions.com/resources/hololens-app-for-oil-and-natural-gas-industry.html (6 pages).

Grey E. "Reality check: augmented and virtual technology in the mining industry" Mining Technology; Jun. 27, 2016; Retrieved from the Internet: URL: https://www.mining-technology.com/features/featurereality-check-augmented-and-virtual-technology-in-the-mining-industry-4913055/ (9 pages).

First Examination Report issued in corresponding Saudis Application No. 122440786, mailed Sep. 19, 2024 (7 pages).

* cited by examiner

INTERACTIVE CORE DESCRIPTION ASSISTANT USING VIRTUAL REALITY

BACKGROUND

A core is a cylindrical section of recovered drilled sediments of rocks. A core sample is a piece of sediment rock recovered from the drilled core. The core interval corresponds to a depth range in the drilled sediment of rocks. The cylindrical section resembles a column in shape and is also referred to as a rock core column. Core samples are usually obtained by drilling with a coring bit (e.g., hollow steel tube) into the sediment or rocks. Core samples are used for analysis of porosity, permeability, fluid saturation, among other compositional and textural rock properties. Sedimentology encompasses the study of modern sediments such as sand, silt, and clay, and the processes that result in their formation, transport, deposition, and diagenesis. Sedimentologists apply their understanding of modern processes to interpret geologic history through observations of sedimentary rocks and sedimentary structures.

Core description is a lengthy process to acquire geological information from physical core samples that consumes a lot of sedimentologists' time (e.g., one or more days) to log and describe a full recovered core. In making urgent and critical decision in dynamic exploration environment, waiting even one day to get the answer from core description will contribute to the increase of exploration risk.

Conventional core description is conducted using primarily the physical core sample. The sedimentologist visually screens the entire core sample to identify the core feature needed to be reported in the core description document or to construct a deposition model. In this process the sedimentologist may neglect a tremendous volume of data directly or indirectly related to the physical core, such as thin section, SEM images, wireline logs, drilling logs, conventional and special core analysis, core gamma ray, etc. These data are neglected not because of their irrelevance to the core description process, but due to lack of technology to allow simultaneous viewing of this data and the physical core sample.

Augmented Reality (AR) allows a user to interact with a computer-generated output overlaid on or around objects in a real-world environment. The real-world environment augmented by the overlaying computer-generated output is referred to as the AR environment. In other words, the AR environment is the combination of the real-world environment and the overlaying computer-generated output. An AR device is a device used by the user to interact with the AR environment. For example, the AR device may include an optical projector to project an image of the a computer-generated output onto the objects in the real-work environment. In this case, the AR device allows the user to view the combination of the real-world environment and the overlaying computer-generated output by directly viewing the objects in the real-work environment. In another example, the AR device may include an image capturing device (e.g., camera, video camera, etc.) for capturing an image of the objects in the real-work environment and a display device for displaying the computer-generated output superimposed with the captured image. In this case, the AR device allows the user to view the combination of the real-world environment and the overlaying computer-generated output by viewing the display of the AR device. In either case, the view of the combination of the real-world environment and the overlaying computer-generated output is referred to as an AR image presented to the user by the AR device.

SUMMARY

In general, in one aspect, the invention relates to a method for generating a core description. The method includes coring and collecting rock cores from a plurality of geographical locations in the subterranean formation, wherein each of the rock cores is physically tagged with an identifying tag, detecting, using an augmented reality (AR) device worn by a user, content of the identifying tag of a rock core within a device view of the AR device, wherein the content identifies a well where the rock core is obtained, retrieving, by the AR device from a data repository, historical data of the well, activating, by the AR device, a sensor to acquire additional data from the rock core to supplement the historical data, and presenting, by the AR device for viewing by the user, an AR image comprising a first image of the historical data and the additional data superimposed over a second image of the rock core, wherein the user generates the core description based on viewing the AR image.

In general, in one aspect, the invention relates to a, augmented reality (AR) device for generating a core description. The AR device includes a processor and a memory coupled to the processor and storing instruction. The instructions, when executed by the processor, includes functionality for detecting, when the AR device is worn by a user, content of an identifying tag of a rock core within a device view of the AR device, wherein the content identifies a well where the rock core is obtained, retrieving, from a data repository, historical data of the well, activating a sensor to acquire additional data from the rock core to supplement the historical data, and presenting, for viewing by the user, an AR image comprising a first image of the historical data and the additional data superimposed over a second image of the rock core, wherein the user generates the core description based on viewing the AR image.

In general, in one aspect, the invention relates to a system for generating a core description. The system includes a data repository comprising historical data of a plurality of wells, a plurality of rock cores obtained from the plurality of wells, and an augmented reality (AR) device having functionality for detecting, when the AR device is worn by a user, content of an identifying tag of a rock core within a device view of the AR device, wherein the content identifies a well where the rock core is obtained, retrieving, from a data repository, historical data of the well, activating a sensor to acquire additional data from the rock core to supplement the historical data, and presenting, for viewing by the user, an AR image comprising a first image of the historical data and the additional data superimposed over a second image of the rock core, wherein the user generates the core description based on viewing the AR image.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method and a system of an augmented reality (AR) device for generating a core description. Initially, rock cores are collected from various geographical locations in a subterranean formation, where each rock core is physically tagged with an identifying tag. In one or more embodiments of the invention, an AR device worn by a user is used to detect content of the identifying tag of a rock core within a device view of the AR device. The device view is a field-of-view of an image capture device or an image projection device of the AR device. The content identifies a well where the rock core is obtained. Accordingly, the AR device retrieves historical data of the well from a data repository. In one or more embodiments, the AR device determines that additional data is needed to supplement the historical data and activates a sensor to acquire such additional data from the rock core. An AR image is then generated by the AR device that includes an image of the historical data and the additional data collectively, which is projected onto the physical rock core or superimposed over a rock core image captured by the AR device. The AR image is presented by the AR device for viewing by the user such that the user generates the core description based on viewing the AR image.

Figure 1:
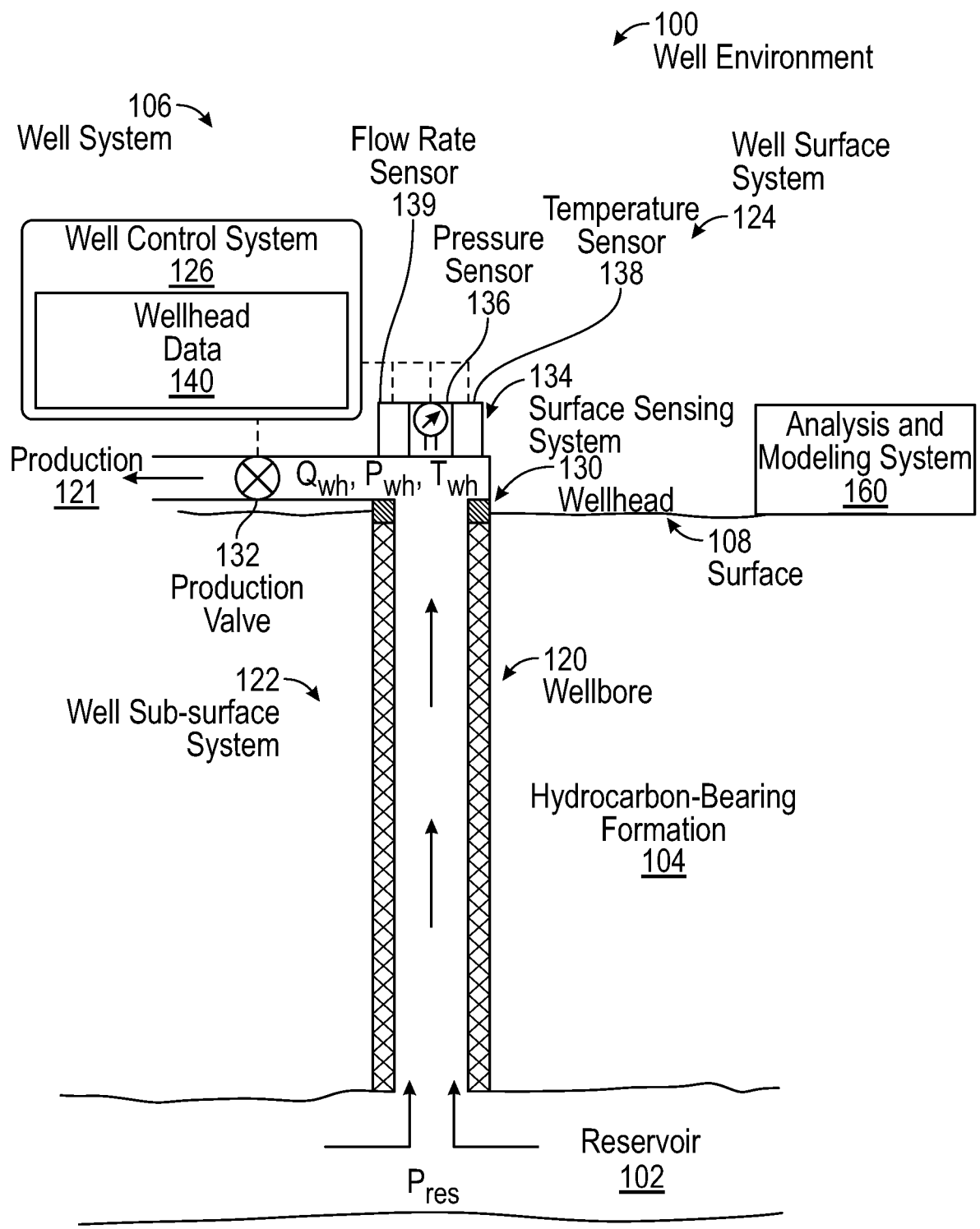
FIGS. 1 and 2 show systems in accordance with one or more embodiments.

Turning to FIG. 1, FIG. 1 shows a schematic diagram in accordance with one or more embodiments. As shown in FIG. 1, FIG. 1 illustrates a well environment (100) that includes a hydrocarbon reservoir ("reservoir") (102) located in a subsurface hydrocarbon-bearing formation ("formation") (104) and a well system (106). The hydrocarbon-bearing formation (104) may include a porous or fractured rock formation that resides underground, beneath the earth's surface ("surface") (108). In the case of the well system (106) being a hydrocarbon well, the reservoir (102) may include a portion of the hydrocarbon-bearing formation (104). The hydrocarbon-bearing formation (104) and the reservoir (102) may include different layers of rock having varying characteristics, such as varying degrees of permeability, porosity, capillary pressure, and resistivity. In the case of the well system (106) being operated as an exploratory well, a coring operation may be performed to collect rock samples (referred to as core samples) from the wellbore (120) for analysis by a sedimentologist or other geoscientist. In the case of the well system (106) being operated as a production well, the well system (106) may facilitate the extraction of hydrocarbons (or "production") from the reservoir (102).

In some embodiments, the well system (106) includes the wellbore (120), a well sub-surface system (122), a well surface system (124), a well control system ("control system") (126), and an analysis and modeling system (160). The control system (126) may control various operations of the well system (106), such as well production operations, well completion operations, well maintenance operations, and reservoir monitoring, assessment and development operations. In some embodiments, the control system (126) includes a computer system that is the same as or similar to that of computer system (500) described below in FIG. 5 and the accompanying description.

The wellbore (120) may include a bored hole that extends from the surface (108) into a target zone of the hydrocarbon-bearing formation (104), such as the reservoir (102). An upper end of the wellbore (120), terminating at or near the surface (108), may be referred to as the "up-hole" end of the wellbore (120), and a lower end of the wellbore, terminating in the hydrocarbon-bearing formation (104), may be referred to as the "down-hole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the hydrocarbon-bearing formation (104) or the reservoir (102) during injection operations, or the communication of monitoring devices (e.g., logging tools) into the hydrocarbon-bearing formation (104) or the reservoir (102) during monitoring operations (e.g., during in situ logging operations).

In some embodiments, during operation of the well system (106), the control system (126) collects and records wellhead data (140) for the well system (106). The wellhead data (140) may include, for example, a record of measurements of wellhead pressure ($P_{wh}$) (e.g., including flowing wellhead pressure), wellhead temperature ($T_{wh}$) (e.g., including flowing wellhead temperature), wellhead production rate ($Q_{wh}$) over some or all of the life of the well (106), and water cut data. In some embodiments, the measurements are recorded in real-time, and are available for review or use within seconds, minutes or hours of the condition being sensed (e.g., the measurements are available within 1 hour of the condition being sensed). In such an embodiment, the wellhead data (140) may be referred to as "real-time" wellhead data (140). Real-time wellhead data (140) may enable an operator of the well (106) to assess a relatively current state of the well system (106), and make real-time decisions regarding development of the well system (106) and the reservoir (102), such as on-demand adjustments in regulation of production flow from the well.

In some embodiments, the well sub-surface system (122) includes casing installed in the wellbore (120). For example, the wellbore (120) may have a cased portion and an uncased (or "open-hole") portion. The cased portion may include a portion of the wellbore having casing (e.g., casing pipe and casing cement) disposed therein. The uncased portion may include a portion of the wellbore not having casing disposed therein. In some embodiments, the casing includes an annular casing that lines the wall of the wellbore (120) to define a central passage that provides a conduit for the transport of tools and substances through the wellbore (120). For example, the central passage may provide a conduit for lowering logging tools into the wellbore (120), a conduit for the flow of production (121) (e.g., oil and gas) from the reservoir (102) to the surface (108), or a conduit for the flow of injection substances (e.g., water) from the surface (108) into the hydrocarbon-bearing formation (104). In some embodiments, the well sub-surface system (122) includes production tubing installed in the wellbore (120). The production tubing may provide a conduit for the transport of tools and substances through the wellbore (120). The production tubing may, for example, be disposed inside casing. In such an embodiment, the production tubing may provide a conduit for some or all of the production (121) (e.g., oil and gas) passing through the wellbore (120) and the casing.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more production valves (132) that are operable to control the flow of production (134). For example, a production valve (132) may be fully opened to enable unrestricted flow of production (121) from the wellbore (120), the production valve (132) may be partially opened to partially restrict (or "throttle") the flow of production (121) from the wellbore (120), and production valve (132) may be fully closed to fully restrict (or "block") the flow of production (121) from the wellbore (120), and through the well surface system (124).

In some embodiments, the wellhead (130) includes a choke assembly. For example, the choke assembly may include hardware with functionality for opening and closing the fluid flow through pipes in the well system (106). Likewise, the choke assembly may include a pipe manifold that may lower the pressure of fluid traversing the wellhead. As such, the choke assembly may include set of high pressure valves and at least two chokes. These chokes may be fixed or adjustable or a mix of both. Redundancy may be provided so that if one choke has to be taken out of service, the flow can be directed through another choke. In some embodiments, pressure valves and chokes are communicatively coupled to the well control system (126). Accordingly, a well control system (126) may obtain wellhead data regarding the choke assembly as well as transmit one or more commands to components within the choke assembly in order to adjust one or more choke assembly parameters.

Keeping with FIG. 1, in some embodiments, the well surface system (124) includes a surface sensing system (134). The surface sensing system (134) may include sensors for sensing characteristics of substances, including production (121), passing through or otherwise located in the well surface system (124). The characteristics may include, for example, pressure, temperature and flow rate of production (121) flowing through the wellhead (130), or other conduits of the well surface system (124), after exiting the wellbore (120).

In some embodiments, the surface sensing system (134) includes a surface pressure sensor (136) operable to sense the pressure of production (151) flowing through the well surface system (124), after it exits the wellbore (120). The surface pressure sensor (136) may include, for example, a wellhead pressure sensor that senses a pressure of production (121) flowing through or otherwise located in the wellhead (130). In some embodiments, the surface sensing system (134) includes a surface temperature sensor (138) operable to sense the temperature of production (151) flowing through the well surface system (124), after it exits the wellbore (120). The surface temperature sensor (138) may include, for example, a wellhead temperature sensor that senses a temperature of production (121) flowing through or otherwise located in the wellhead (130), referred to as "wellhead temperature" ($T_{wh}$). In some embodiments, the surface sensing system (134) includes a flow rate sensor (139) operable to sense the flow rate of production (151) flowing through the well surface system (124), after it exits the wellbore (120). The flow rate sensor (139) may include hardware that senses a flow rate of production (121) ($Q_{wh}$) passing through the wellhead (130).

In some embodiments, the well system (106) includes an analysis and modeling system (160). For example, the analysis and modeling system (160) may include hardware and/or software with functionality for generating and presenting augmented reality images of rock cores to facilitate a user in generating core description reports. For example, the user may be a sedimentologist or other geoscientist. While the analysis and modeling system (160) is shown at a well site, embodiments are contemplated where the analysis and modeling system (160) are located away from well sites. In some embodiments, the analysis and modeling system (160) may include a computer system that is similar to the computer system (500) described below with regard to FIG. 5 and the accompanying description.

Figure 2:
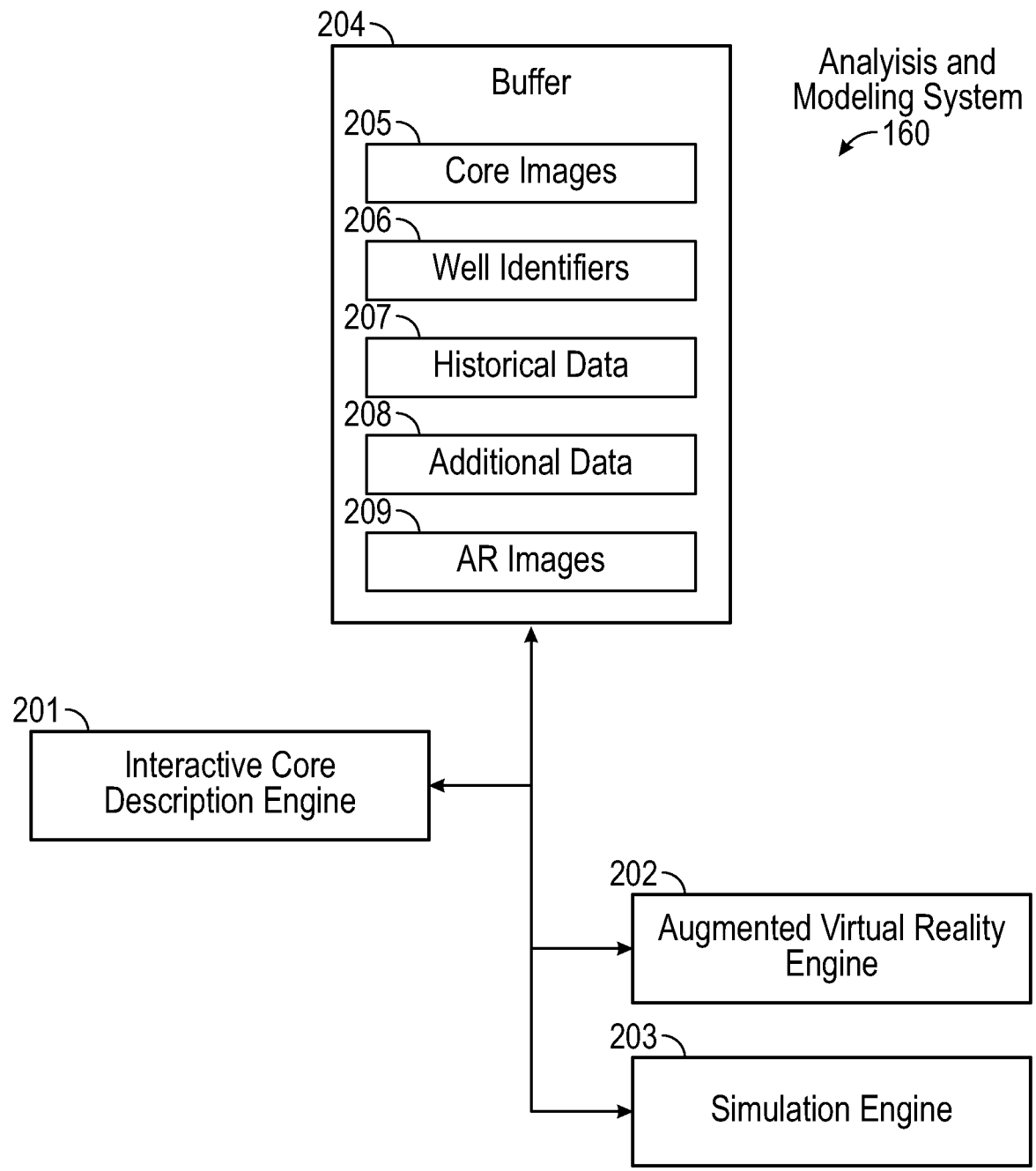

Turning to FIG. 2, FIG. 2 shows a schematic diagram in accordance with one or more embodiments. In one or more embodiments, one or more of the modules and/or elements shown in FIG. 2 may be omitted, repeated, and/or substituted. Accordingly, embodiments of the disclosure should not be considered limited to the specific arrangements of modules and/or elements shown in FIG. 2.

FIG. 2 illustrates the analysis and modeling system (160) that has multiple components, including, for example, a buffer (204), an interactive core description engine (201), an augmented virtual reality engine (202), and a simulation engine (203). Each of these components (201, 202, 203, 204) may be located and executed on a same computing device (e.g., a dedicated AR device or a general purpose personal computer (PC), laptop, tablet PC, smart phone, multifunction printer, kiosk, server, etc.) or on different computing devices that are connected via a network, such as a wide area network or a portion of Internet of any size having wired and/or wireless segments. In some embodiments, components of the analysis and modeling system (160) reside in an integrated AR device. In other embodiments, components of the analysis and modeling system (160) reside in a combination of the AR device and other computing devices such as a remote server connected via the network. For example, the AR device may include an image capture device (e.g., a camera or video camera), a sensor (e.g., a hyperspectral camera, Lidar (laser detection and ranging)), and an image projection device. In another example, the AR device may include an image capture device (e.g., a camera or video camera), a sensor (e.g., a hyperspectral camera, Lidar), and a display device. Specifically, the AR device may be a wearable AR glasses where the display device is a goggle with built-in LED display screen. In addition, the AR environment may include real-work objects such as core samples. For example, the AR device may be used by a sedimentologist or other geoscientist to view the core samples with overlaying computer generated output. Each of these components of the analysis and modeling system (160) is discussed below.

In one or more embodiments of the invention, the buffer (204) may be implemented in hardware (i.e., circuitry), software, or any combination thereof. The buffer (204) is configured to store data generated and/or used by the analysis and modeling system (160). For example, a portion of the buffer (204) may reside in a data repository connected to the AR device where historical data stored in the data repository may be accessed by the AR device. In another example, a portion of the buffer (204) may reside in the AR device directly accessible by the AR device. The data stored in the buffer (204) includes core images (205), well identifiers (206), historical data (207), additional data (208), and AR images (209).

The core images (205) are high resolution photographs of rock cores. The core images (205) include photographs of a number of rock core columns collected from different well locations throughout an area of interest. Each rock core column is a sequence of rock cores extending across a depth range of interest in the borehole of a particular well. In particular, each rock core is marked to indicate the depths in the particular well such that the depth markings and well identification (collectively referred to as a depth tag) are captured in the corresponding core image. Alternatively or in addition, the depth information and well identification are encoded in a radio frequency identification (RFID) tag attached to the rock core. In one or more embodiments of the invention, the core images (205) are captured using a camera of an augmented reality (AR) device. The width of each of core image (205) corresponds to the cylindrical circumference of the rock core column, or a portion of the circumference. In an example scenario, a core image corresponds to a portion of the length of a rock core. In another example, a core image may correspond to the length of two or more consecutive rock cores in the rock core column.

The well identifiers (206) are information retrieved from the imaged depth tags or from the RFID attached to the rock cores.

The historical data (207) are previously acquired data about the particular well pertaining to the depths of corresponding rock cores, such as well log, thin section images of the rock cores, and existing core description logs.

The additional data (208) is any data of interest related to the corresponding rock cores that is not contained in the historical data (206). For example, the additional data (208) may include data acquired by a sensor of the AR device. The additional data (208) may include color, grain size/texture, hydrocarbon shows, bitumen staining, fractures, bedding surfaces, laminations, cross-bedding, erosional surfaces, lithology changes, bioturbation, limestone texture, stylolites, hydrothermal dolomitization using both light detection and Lidar ranging, etc.

The AR images (209) are synthesized images generated by the AR device. Each AR image combines an image representing the historical data and additional data related to the corresponding rock core as well as a rock core image captured by the AR device from the rock core. The rock core image is one of the core images (205). The AR device includes a processor in order to synthesize images to obtain AR images (209).

In one or more embodiments, the interactive core description engine (201), the augmented virtual reality engine (202), and the simulation engine (203) may be implemented in hardware (i.e., circuitry), software, or any combination thereof. For example, a portion of these engines (e.g., the interactive core description engine (201), the augmented virtual reality engine (202), or portions thereof) may reside in the AR device, while other portions of the engines (e.g., the simulation engine (203)) may reside in the remote server.

In one or more embodiments, the interactive core description engine (201) is configured to interact with the user to enable/disable the AR device, manually activate/deactivate the sensor of the AR device, select historical data from a data repository, select an AR image format for viewing, among other augmented reality control functions. In addition, the interactive core description engine (201) facilitates generation of the core description by a user while the user is viewing the AR image (209).

In one or more embodiments, the augmented virtual reality engine (202) is configured to generate and present the AR image (209) based on the core images (205), well identifiers (206), historical data (207), and additional data (209). For example, the AR image (209) may be presented on a display screen of the AR device for viewing by the user. In another example, the AR image (209) may be projected by the AR device onto the core samples for viewing by the user.

In one or more embodiments, the simulation engine (203) is configured to generate one or more models regarding the hydrocarbon-bearing formation (104) and/or performing one or more simulations based on the models. For example, the simulation engine (203) may store or access core descriptions and other data regarding core samples to/from the buffer (204) for performing simulations. For example, the core descriptions and other data accessible by the simulation engine (203) may be from previously described core samples from the same or similar formations. The simulation engine (203) may further analyze the well log data, the core sample data, seismic data, and/or other types of data to generate and/or update the one or more models. The simulation results generated by the simulation engine (203) may be used to facilitate various field operations performed for the well environment (100) depicted in FIG. 1 above.

In one or more embodiments, the analysis and modeling system (160) performs the functionalities described above using the method described in reference to FIG. 3 below. Although the analysis and modeling system (160) is shown as having three engines (201, 202, 203), in other embodiments of the invention, the analysis and modeling system (160) may have more or fewer engines and/or more or fewer other components. Further, the functionality of each component described above may be split across components. Further still, each component (201, 202, 203) may be utilized multiple times to carry out an iterative operation.

Figure 3:
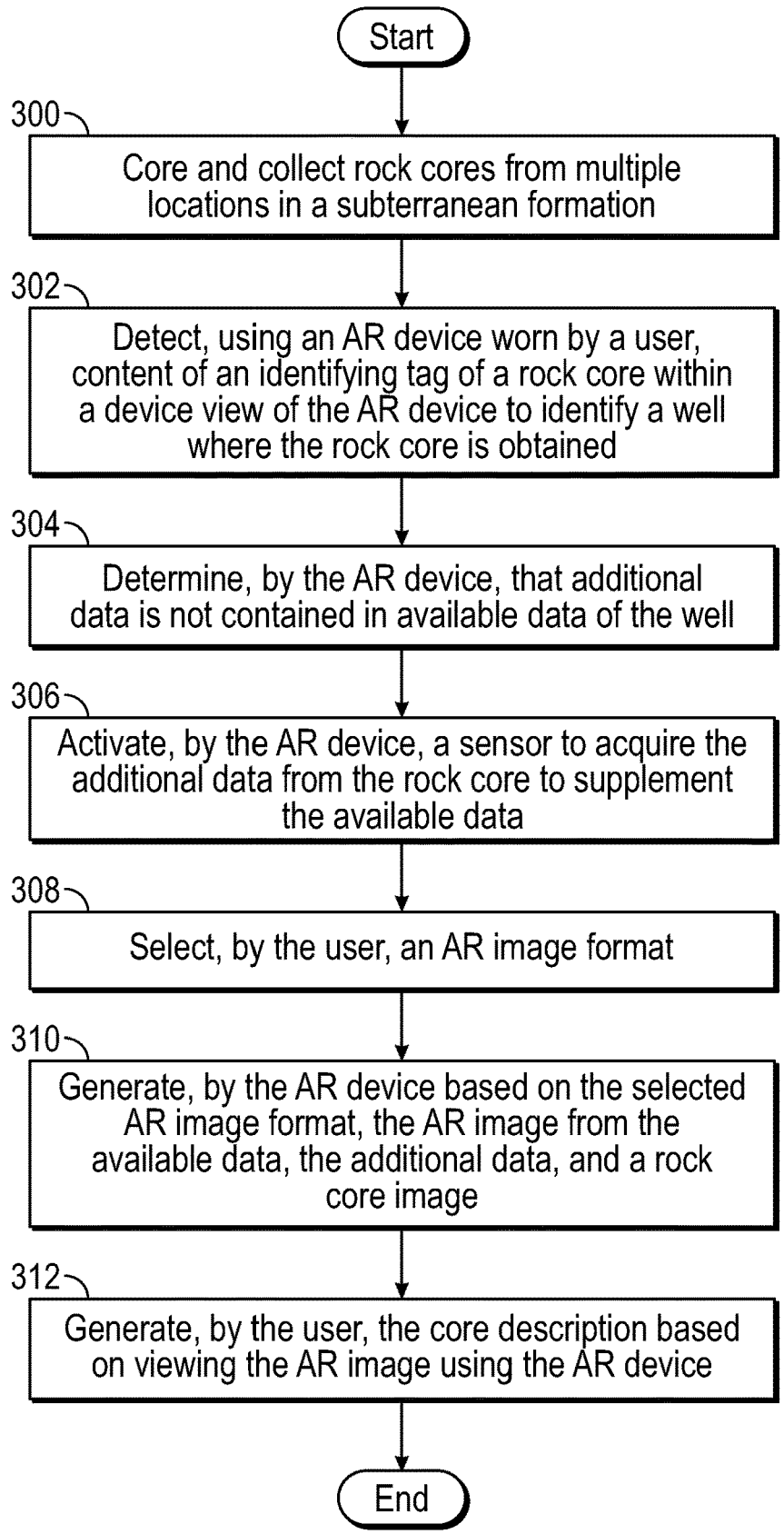
FIG. 3 shows a flowchart in accordance with one or more embodiments.

Turning to FIG. 3, FIG. 3 shows a flowchart in accordance with one or more embodiments. Specifically, FIG. 3 describes a method of generating a core description. One or more blocks in FIG. 3 may be performed using one or more components as described in FIGS. 1 and 2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Initially in Block 300, coring is performed to collect rock cores from a number of geographical locations in one or more subterranean formations. The rock cores are laid out in a sequential order to form a contiguous column (referred to as a rock core column) according to respective depths where the rock cores are collected. One rock core column is laid out for each of the geographical locations where coring is performed.

In Block 302, using an augmented reality (AR) device worn by a user, content of an identifying tag of a rock core within a device view of the AR device is detected. The identifying tag may be one of a radio frequency identification (RFID) tag and a depth tag. The content of the identifying tag identifies a well where the rock core is obtained. In one or more embodiments, the AR device is automatically connected to a data repository in response to detecting the user wearing the AR device. Accordingly, the AR device retrieves from data repository historical data of the well that includes one or more of a well log, a thin section image, and a digitized core description log.

In Block 304, it is determined by the AR device that additional data regarding the rock core is needed that is not contained in historical data of the well. In one or more embodiments, AI or machine learning techniques are used by the AR device to make this determination. For example, the AI or machine learning techniques may include K-NN (nearest neighbors) machine learning algorithm, regression in random forest, convolutional neural networks (CNN), etc.

In Block 306, the AR device activates a sensor to acquire additional data from the rock core to supplement the historical data. In one or more embodiments, the AR device identifies a type of the additional data and selects the sensor that is capable of acquiring the identified type of the additional data. Accordingly, the AR device activates the sensor that is suitable to acquire the additional data. In one or more embodiments, artificial intelligence (AI) algorithms are applied to raw information acquired by the sensor from the rock core to generate the additional data. As noted above, the AI or machine learning techniques may include K-NN (nearest neighbors) machine learning algorithm, regression in random forest, convolutional neural networks (CNN), etc. The raw information acquired by the sensor may include color, grain size/texture, hydrocarbon shows, bitumen staining, fractures, bedding surfaces, laminations, cross-bedding, erosional surfaces, lithology changes, bioturbation, limestone texture, stylolites, hydrothermal dolomitization using both light detection and Lidar ranging, etc.

In Block 308, an AR image format is selected by the user, such as a display format, a visualization format, and an overlay format. For example, the AR device may present a graphical user interface viewable by the user for selecting the AR image format.

In Block 310, the AR device generates, based on the selected AR image format, the AR image from the historical data, the additional data, and a rock core image that is captured by the AR device while the rock core is in the device view. The AR image is presented by the AR device for viewing by the user. In one or more embodiments, an image of the historical data and the additional data is superimposed over the rock core image of the rock core to generate the AR image.

In Block 312, the core description is generated by the user based on viewing the AR image.

Figure 4A:
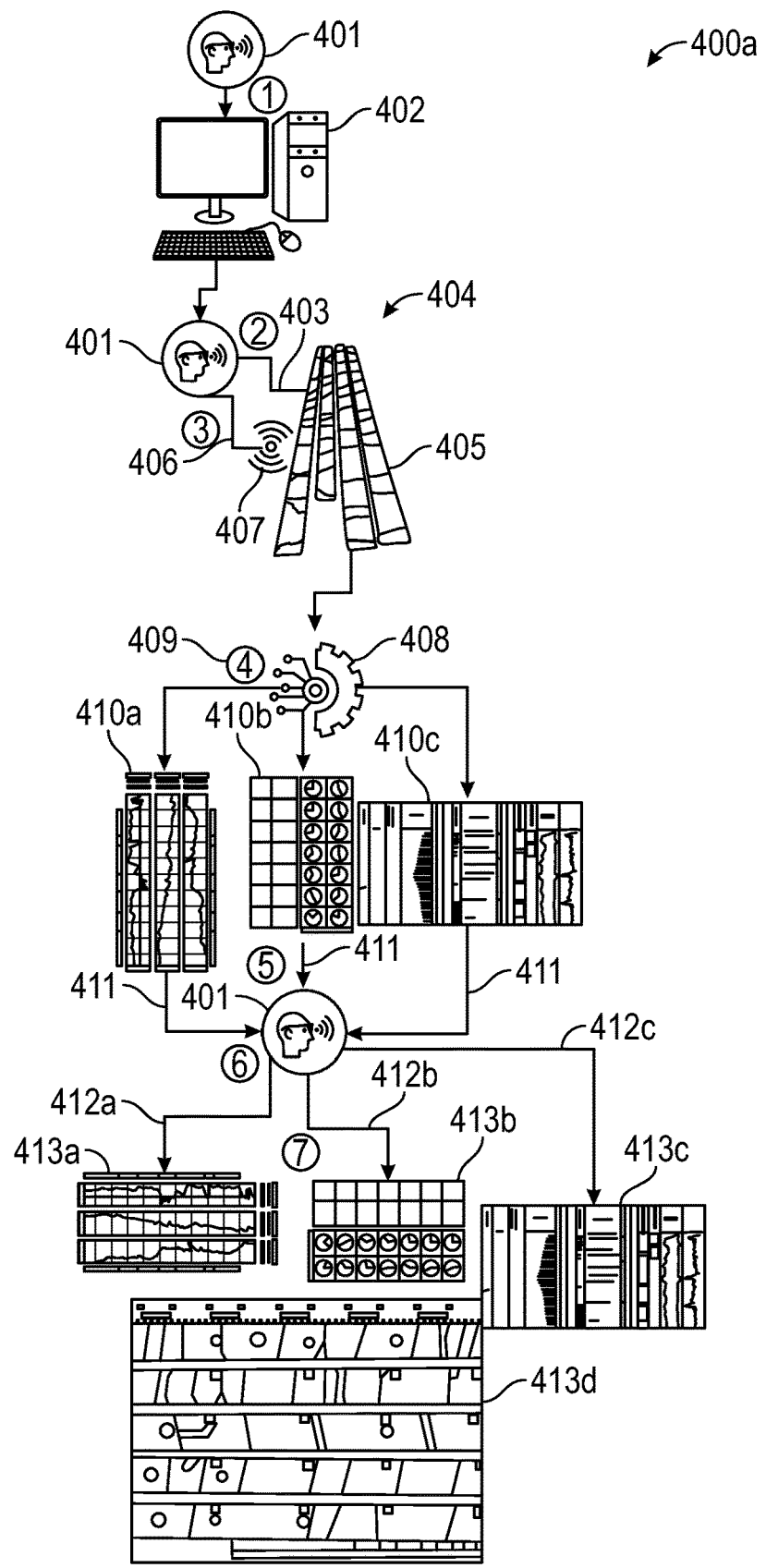
FIGS. 4A and 4B show an example of AR device interaction in accordance with one or more embodiments.
Figure 4B:
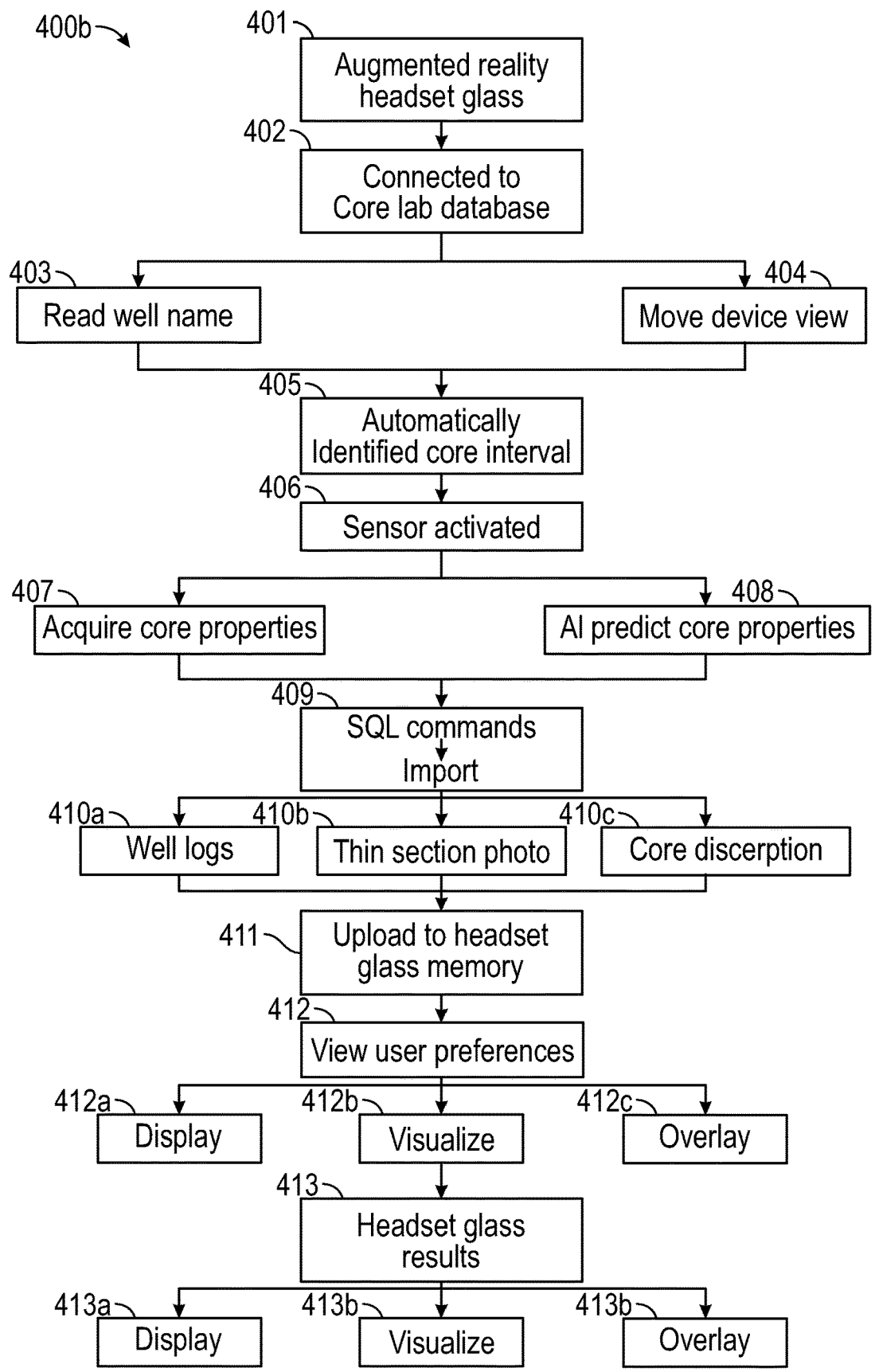

Turning to FIGS. 4A-4B, FIGS. 4A-4B provide an example of the interactive core description assistant with virtual reality. In particular, FIG. 4A presents the example as a schematic diagram (400a) while FIG. 4B presents the example as a flowchart (400b). The example shown in FIGS. 4A-4B may be, for example, based on one or more components depicted in FIGS. 1-2 above and the method flowchart depicted in FIG. 3 above. In one or more embodiments, one or more of the modules and/or elements shown in FIGS. 4A-4B may be omitted, repeated, and/or substituted. Accordingly, embodiments disclosed herein should not be considered limited to the specific arrangements of modules and/or elements shown in FIGS. 4A-4B.

As shown in FIGS. 4A-4B, the example involves augmented reality headset glasses (401) that provides live view and visualization through optic lenses to automate overlaying well logs, thin section images and digital core retrieved from a core lab database (402). The augmented reality headset glasses, an example of the aforementioned AR device, is a smart user wearable device that displays 3D holograms overlaid on the real world where the user is located to render a mixed reality experience to the user. For example, the sedimentologist wears the augmented reality headset glasses and chooses to display, overlay or visualize the well logs, thin section and digital core description that superimpose physical core samples. In this manner, the core visualization environment is enhanced to minimize the time spent on core description thus allow rapid exploration decision. Furthermore, the enhanced the core visualization environment also improves the training experience of any sedimentologist under training.

Initially in the schematic diagram (400a), the augmented reality headset glasses (401) worn by the sedimentologist is connected to the core lab database (402) and reads well name (403) using core sample RIFD code. The core sample RIFD code identifies the particular well where the core sample is obtained.

Next in the schematic diagram (400a), the sedimentologist moves the augmented reality headset glasses (401) to orient the device view (404) from one core to another. The device view (404) is a field-of-view of the augmented reality headset glasses (401) as seen by the sedimentologist. As the augmented reality headset glasses (401) moves, the core interval within the device view (404) is automatically identified either from the core sample RFID or a depth tag on the core. The core interval identifies the depth range in the well that corresponds to the length of the core. Based on the core sample RFID or the depth tag on the core, previously acquired data in the core lab database (402) corresponding to the depth range is identified. Any well logs, thin section photo and digitized core description log that may be missing in the core lab database (402) corresponding to the depth range is also identified.

Next in the schematic diagram (400a), a sensor (e.g., a hyperspectral camera, Lidar) mounted on the augmented reality headset glasses (401) is activated by the sedimentologist to acquire additional data (i.e., new data) from the core sample or the core interval within the device view (404). The sensor may be activated in response to an input from the sedimentologist, or activated automatically in response to detecting, based on the RFID or the depth tag, any missing well logs, thin section photo and/or digitized core description log that is not contained in the core lab database (402). Once new data is acquired by the sensor, artificial intelligence (AI) can be applied to predict certain core properties of the core sample based on the new data.

Next in the schematic diagram (400a), the existing data associated with core interval, such as well logs, thin section photo and digitized core description log, are selected by user for retrieval from the core lab database (402).

Next in the schematic diagram (400a), the augmented reality headset glasses (401) load the selected existing data to its memory to be ready for display, visualize and/or overlay. Display refers to exhibiting the digital core data on computer screen or projector. Visualize refers to envisioning the digital core data in one dimension (1D), two dimensions (2D) or three dimensions (3D). Overlay refers to displaying the image of digital core data on top of actual core interval for correlation purposes.

Next in the schematic diagram (400*a*), the sedimentologist is allowed to select and order the augmented reality headset glasses (401) to select the preferred view (i.e., display, visualize, or overlay) of data to be displayed, visualized or overlaid or combination by several views. The preferred view corresponds to the aforementioned AR image format.

Next in the schematic diagram (400*a*), once the preferred view is selected, the augmented reality headset glasses (401) is used by the sedimentologist to view the preferred view of data superimposed on top of the core within the device view (404).

By viewing the overlaid well logs, thin section photo visualize digital core instantaneously on laid-down core, the invention provides the advantages to (i) accelerate the core description process, (ii) reduce exploration risk and enhance exploration management decision, (iii) export and import digital core/cutting description, and (iv) create core visualization environment for core description and training.

Figure 5:
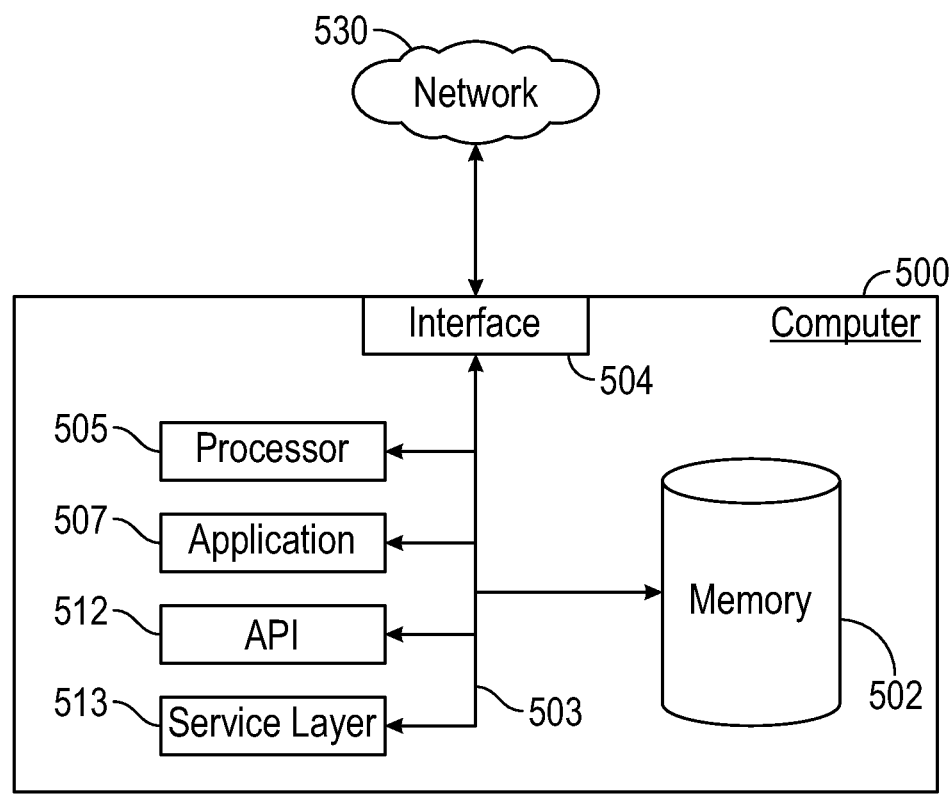
FIG. 5 shows a computing system in accordance with one or more embodiments.

Embodiments may be implemented on a computer system. FIG. 5 is a block diagram of a computer system (500) used to provide computational functionalities associated with described algorithms, methods, functions, processes, flows, and procedures as described in the instant disclosure, according to an implementation. The illustrated computer (500) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (500) may include a computer that includes an input device, such as a keypad, keyboard, touch screen, or other device that can accept user information, and an output device that conveys information associated with the operation of the computer (500), including digital data, visual, or audio information (or a combination of information), or a GUI.

The computer (500) can serve in a role as a client, network component, a server, a database or other persistency, or any other component (or a combination of roles) of a computer system for performing the subject matter described in the instant disclosure. The illustrated computer (500) is communicably coupled with a network (530). In some implementations, one or more components of the computer (500) may be configured to operate within environments, including cloud-computing-based, local, global, or other environment (or a combination of environments).

At a high level, the computer (500) is an electronic computing device operable to receive, transmit, process, store, or manage data and information associated with the described subject matter. According to some implementations, the computer (500) may also include or be communicably coupled with an application server, e-mail server, web server, caching server, streaming data server, business intelligence (BI) server, or other server (or a combination of servers).

The computer (500) can receive requests over network (530) from a client application (for example, executing on another computer (500)) and responding to the received requests by processing the said requests in an appropriate software application. In addition, requests may also be sent to the computer (500) from internal users (for example, from a command console or by other appropriate access method), external or third-parties, other automated applications, as well as any other appropriate entities, individuals, systems, or computers.

Each of the components of the computer (500) can communicate using a system bus (503). In some implementations, any or all of the components of the computer (500), both hardware or software (or a combination of hardware and software), may interface with each other or the interface (504) (or a combination of both) over the system bus (503) using an application programming interface (API) (512) or a service layer (513) (or a combination of the API (512) and service layer (513). The API (512) may include specifications for routines, data structures, and object classes. The API (512) may be either computer-language independent or dependent and refer to a complete interface, a single function, or even a set of APIs. The service layer (513) provides software services to the computer (500) or other components (whether or not illustrated) that are communicably coupled to the computer (500). The functionality of the computer (500) may be accessible for all service consumers using this service layer. Software services, such as those provided by the service layer (513), provide reusable, defined business functionalities through a defined interface. For example, the interface may be software written in JAVA, C++, or other suitable language providing data in extensible markup language (XML) format or other suitable format. While illustrated as an integrated component of the computer (500), alternative implementations may illustrate the API (512) or the service layer (513) as stand-alone components in relation to other components of the computer (500) or other components (whether or not illustrated) that are communicably coupled to the computer (500). Moreover, any or all parts of the API (512) or the service layer (513) may be implemented as child or sub-modules of another software module, enterprise application, or hardware module without departing from the scope of this disclosure.

The computer (500) includes an interface (504). Although illustrated as a single interface (504) in FIG. 5, two or more interfaces (504) may be used according to particular needs, desires, or particular implementations of the computer (500). The interface (504) is used by the computer (500) for communicating with other systems in a distributed environment that are connected to the network (530). Generally, the interface (504) includes logic encoded in software or hardware (or a combination of software and hardware) and operable to communicate with the network (530). More specifically, the interface (504) may include software supporting one or more communication protocols associated with communications such that the network (530) or interface's hardware is operable to communicate physical signals within and outside of the illustrated computer (500).

The computer (500) includes at least one computer processor (505). Although illustrated as a single computer processor (505) in FIG. 5, two or more processors may be used according to particular needs, desires, or particular implementations of the computer (500). Generally, the computer processor (505) executes instructions and manipulates data to perform the operations of the computer (500) and any algorithms, methods, functions, processes, flows, and procedures as described in the instant disclosure.

The computer (500) also includes a memory (506) that holds data for the computer (500) or other components (or a combination of both) that can be connected to the network (530). For example, memory (506) can be a database storing data consistent with this disclosure. Although illustrated as a single memory (506) in FIG. 5, two or more memories may be used according to particular needs, desires, or particular implementations of the computer (500) and the described functionality. While memory (506) is illustrated as an integral component of the computer (500), in alternative implementations, memory (506) can be external to the computer (500).

The application (507) is an algorithmic software engine providing functionality according to particular needs, desires, or particular implementations of the computer (500), particularly with respect to functionality described in this disclosure. For example, application (507) can serve as one or more components, modules, applications, etc. Further, although illustrated as a single application (507), the application (507) may be implemented as multiple applications (507) on the computer (500). In addition, although illustrated as integral to the computer (500), in alternative implementations, the application (507) can be external to the computer (500).

There may be any number of computers (500) associated with, or external to, a computer system containing computer (500), each computer (500) communicating over network (530). Further, the term "client," "user," and other appropriate terminology may be used interchangeably as appropriate without departing from the scope of this disclosure. Moreover, this disclosure contemplates that many users may use one computer (500), or that one user may use multiple computers (500).

In some embodiments, the computer (500) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method for generating a core description, the method comprising:
    coring and collecting rock cores from a plurality of geographical locations in a well environment, wherein each of the rock cores is physically tagged with an identifying tag;
    detecting, using an augmented reality (AR) device worn by a user, content of the identifying tag of a rock core within a device view of the AR device, wherein the content identifies a well where the rock core is obtained;
    retrieving, by the AR device from a data repository, historical well log data acquired using a logging tool of the well, wherein the historical well log data is not acquired from the rock core;
    activating, by the AR device, a sensor to acquire additional data from the rock core to supplement the historical data;
    presenting, by the AR device for viewing by the user, an AR image comprising a first image of the historical well log data not acquired from the rock core and the additional data acquired from the rock core that are superimposed over a second image of the rock core, wherein the user generates the core description based on viewing the AR image; and
    performing, based at least on the core description, a field operation of the well.

2. The method according to claim 1,
    wherein the identifying tag comprises one or more of a radio frequency identification (RFID) tag and a depth tag.

3. The method according to claim 1, further comprising:
    connecting, in response to detecting the user wearing the AR device, the AR device to the data repository.

4. The method according to claim 1, further comprising:
    capturing, by the AR device, the second image of the rock core;
    selecting, by the user, a format of the AR image; and
    generating, by the AR device based on the selected format, the AR image from the historical data, the additional data, and the second image.

5. The method according to claim 1,
    wherein the historical data comprises one or more of a well log, a thin section image, and a digitized core description log.

6. The method according to claim 5, further comprising:
    determining, by the AR device, that the additional data is not contained in the historical data,
    wherein activating the sensor is in response to said determining.

7. The method according to claim 6, further comprising:
    identifying, by the AR device, a type of the additional data; and
    selecting, by the AR device, the sensor that is capable to acquire the identified type of the additional data,
    wherein activating the sensor is further in response to said selecting.

8. An augmented reality (AR) device for generating a core description, comprising:
    a processor; and
    a memory coupled to the processor and storing instruction, the instructions, when executed by the processor, comprising functionality for:

detecting, when the AR device is worn by a user, content of an identifying tag of a rock core within a device view of the AR device, wherein the content identifies a well where the rock core is obtained;

retrieving, from a data repository, historical well log data acquired using a logging tool of the well, wherein the historical well log data is not acquired from the rock core;

activating a sensor to acquire additional data from the rock core to supplement the historical data; and presenting, for viewing by the user, an AR image comprising a first image of the historical well log data not acquired from the rock core and the additional data acquired from the rock core that are superimposed over a second image of the rock core, wherein the user generates the core description based on viewing the AR image, and wherein a field operation of the well is performed based at least on the core description.

9. The AR device according to claim 8, wherein the identifying tag comprises one or more of a radio frequency identification (RFID) tag and a depth tag.

10. The AR device according to claim 8, the instructions, when executed by the processor, further comprising functionality for:

connecting, in response to detecting the user wearing the AR device, the AR device to the data repository.

11. The AR device according to claim 8, the instructions, when executed by the processor, further comprising functionality for:

capturing the second image of the rock core;

receiving, from the user, a selected format of the AR image; and generating, based on the selected format, the AR image from the historical data, the additional data, and the second image.

12. The AR device according to claim 8, wherein the historical data comprises one or more of a well log, a thin section image, and a digitized core description log.

13. The AR device according to claim 12, the instructions, when executed by the processor, further comprising functionality for:

determining that the additional data is not contained in the historical data, wherein activating the sensor is in response to said determining.

14. The AR device according to claim 13, the instructions, when executed by the processor, further comprising functionality for:

identifying a type of the additional data; and selecting the sensor that is capable to acquire the identified type of the additional data, wherein activating the sensor is further in response to said selecting.

15. A system for generating a core description, comprising:

a data repository comprising historical well log data of a plurality of wells in a well environment;

a plurality of rock cores obtained from the plurality of wells; and an augmented reality (AR) device comprising functionality for:

detecting, when the AR device is worn by a user, content of an identifying tag of a rock core within a device view of the AR device, wherein the content identifies a well where the rock core is obtained;

retrieving, from the data repository, the historical well log data acquired using a logging tool of the well, wherein the historical well log data is not acquired from the rock core;

activating a sensor to acquire additional data from the rock core to supplement the historical data; and presenting, for viewing by the user, an AR image comprising a first image of the historical well log data not acquired from the rock core and the additional data acquired from the rock core that are superimposed over a second image of the rock core, wherein the user generates the core description based on viewing the AR image, and wherein a field operation of the well is performed based at least on the core description.

16. The system according to claim 15, wherein the identifying tag comprises one or more of a radio frequency identification (RFID) tag and a depth tag.

17. The system according to claim 15, the AR device further comprising functionality for:

connecting, in response to detecting the user wearing the AR device, the AR device to the data repository.

18. The system according to claim 15, the AR device further comprising functionality for:

capturing the second image of the rock core;

receiving, from the user, a selected format of the AR image; and generating, based on the selected format, the AR image from the historical data, the additional data, and the second image.

19. The system according to claim 15, wherein the historical data comprises one or more of a well log, a thin section image, and a digitized core description log.

20. The system according to claim 19, the AR device further comprising functionality for:

determining that the additional data is not contained in the historical data, identifying, in response to said determining, a type of the additional data; and selecting the sensor that is capable to acquire the identified type of the additional data, wherein activating the sensor is in response to said selecting.

* * * * *